United States Patent [19]

Luzzana

[11] 4,353,867

[45] Oct. 12, 1982

[54] METHOD AND APPARATUS FOR THE DETERMINATION OF SUBSTANCES IN BIOLOGICAL SOLUTIONS BY DIFFERENTIAL PH MEASUREMENT

[76] Inventor: Massimo Luzzana, Via Olgettina 60, Milan, Italy

[21] Appl. No.: 192,204

[22] Filed: Sep. 30, 1980

[51] Int. Cl.³ .................... G01N 33/84; G01N 27/30
[52] U.S. Cl. .................... 422/68; 23/230 B; 204/1 T; 204/195 B; 422/81
[58] Field of Search ............ 422/68, 50, 81; 23/230 B; 204/1 T, 195 B; 324/438

[56] References Cited

U.S. PATENT DOCUMENTS

| | | | |
|---|---|---|---|
| 3,367,849 | 2/1968 | Blaedel et al. | 204/1 |
| 3,591,480 | 7/1971 | Neff et al. | 204/195 |
| 3,763,422 | 10/1973 | MacPhee et al. | 23/230 B |
| 3,874,850 | 4/1975 | Sorensen et al. | 422/81 X |
| 3,920,969 | 11/1975 | Berglas | 23/230 B |
| 3,960,497 | 6/1976 | Acord | 23/230 B |
| 4,003,705 | 1/1977 | Buzza et al. | 422/81 X |
| 4,233,031 | 11/1980 | Matson et al. | 422/68 X |

*Primary Examiner*—Ronald E. Serwin
*Attorney, Agent, or Firm*—Shlesinger, Arkwright, Garvey & Dinsmore

[57] ABSTRACT

A method and apparatus for the determination of the concentration of certain chemical substances such as glucose, urea, enzymes, etc. in biological solutions such as blood, serum, urine, using a technique of differential pH measurement using two pH electrodes, and measuring pH changes in the solutions after the addition of specific reagents, the concentration being determined according to the formula $$[sample] = FCAL \times (\Delta pH_c - \Delta pH_b - \Delta pH_o)$$

wherein [sample] is the concentration of the substance in the sample, FCAL is a calibration factor, $\Delta pH_c$ is the measured pH of the reacted sample, $\Delta pH_b$ is a pH correction for the reaction initiating compound, and $\Delta pH_o$ is a correction for background pH changes.

10 Claims, 6 Drawing Figures

METHOD AND APPARATUS FOR THE DETERMINATION OF SUBSTANCES IN BIOLOGICAL SOLUTIONS BY DIFFERENTIAL PH MEASUREMENT

This invention relates to the fields of analytical chemistry, clinical chemistry and biochemistry wherein electrometric methods using a pH electrode and a reference electrode, such as a calomel or a silver/silver chloride electrode, have heretofore been widely used for the determination of pH in solution.

BACKGROUND OF THE INVENTION

Many substances, especially those found in biological fluids, can be made to react with appropriate reagent(s) in stoichiometric chemical reactions generating products which are optically active. Many methods have been developed for quantitative determination of such substances as glucose, urea, total carbon dioxide, chloride, and the like taking advantage of such reactions. Typically, one or more of the products of such reactions would create a change in the light transmission through the solution, and spectrophotometers have been used to determine the variation in transmitted light, and therefrom calculating, from known molar absorption coefficients, the concentration of the substance of interest. Alternatively, the products of the reaction may be reacted with a color forming agent and a colorimetric analysis may be made to provide a quantitative indication of the substance in the original soluion. Or instead, the reaction may produce heat or the product of the reaction may conduct electrical current. In these latter cases, calorimetric or conductimetric methods have been used for the determination of the concentration of one or several of the chemical substances participating in the chemical reaction.

Many reactions, on the other hand, give rise to the production of an acid or a base, whose ionization leads, in certain pH ranges to the liberation or the uptake of hydrogen ions.

For example, glucose in solution can be transformed by the addition of the enzyme glucose oxidase (GOD), into gluconic acid, according to the reaction $$\text{glucose} \xrightarrow{\text{GOD}} \text{gluconic acid} + H^+ \quad (1)$$

Since reaction (1) can be made to occur in a medium having a known pH value, the determination of $\Delta[H^+]$, i.e., of the number of hydrogen ions liberated in the reaction, can be used to determine stoichiometrically the concentration of glucose, or, in principle, of any other substance producing or absorbing hydrogen ions in solution. However, in order to carry out such reactions it is necessary that the pH value of the medium does not change below or above certain limits. This is assured by the use of buffer solutions, which are a group of substances able to engage themselves into ionization reactions. The theoretical principles underlying such concepts are well known and are exhaustively treated in any textbook relating to the physical chemistry of electrolytic solutions.

In order to determine $\Delta[H^+]$ produced in reaction (1), use can be made of the equation $$d\mathrm{bH} = \beta \times d[H^+] \quad (2)$$

where dpH and $d[H^+]$ are infinitesimal changes in the pH value of the solution caused by an infinitesimal amount of hydrogen ions, and $\beta$ is the so called "buffer value" of the solution. $\beta$, in turn, is a function of the concentration of buffers in solutions, of their respective ionization constants, and of the pH of the solution, according to the equation $$\beta = 2.3 \times \Sigma_{i=1}^{i=n} C(i) \times a_i \times (1 - a_i) \quad (3)$$

where the number of buffer species present in solution, whose individual concentration is $C_{(i)}$, varies between 1 and n. $a_i$ is the fractional ionization of each species, given by the formula $$a_i = 1/(1 + 10^{pK(i) - pH}) \quad (4)$$

wherein pK equals, for each species, $-\log K_{(i)}$, where $K_{(i)}$ is the ionization constant of the buffer component i.

Integration of equation (2) over a definite pH range gives equation (5):

$$\Delta[H^+] = \beta(\mathrm{pH}(l) - \mathrm{pH}(o)) = \beta \Delta \mathrm{pH} \quad (5)$$

In this integration, it is assumed that the titration curve of the solution is a straight line over the pH range investigated. $\Delta[H^+]$ is the number of hydrogen ions, in moles per liter, which are required to change the pH value of the solution between pH(o) and pH(l). Typical values of $\beta$ for biological solutions at pH=7.4 are $\beta = 7.5 \times 10^{-3}$ moles per liter per pH unit (plasma or serum) and $\beta = 30 \times 10^{-3}$ moles per liter per pH unit (whole blood). Thus the amount of hydrogen ions required to change the pH of plasma or blood, by one pH unit is respectively $7.5 \times 10^{-3}$ moles/liter for plasma and $30 \times 10^{-3}$ moles/liter for blood.

According to the present state of the art, pH measurements on whole blood or plasma by a glass and reference electrode combination, using commercially available electrometers, can achieve resolution no better than $\pm 0.001$ pH units, and even then under only ideal laboratory conditions. Application of equation (5) immediately shows that, for this case, it is possible according to the present state of the art, to estimate, by simple pH measurements, hydrogen ion uptake or release with a sensitivity of $7.5 \times 10^{-3} \times 10^{-3} = 7.5 \times 10^{-6}$ moles/liter in undiluted plasma and of $3 \times 10^{-5}$ moles/liter in whole blood. Since the concentration of many metabolites of clinical interest in biological fluids lies in the concentration range of 5 to $0.1 \times 10^{-3}$ moles/liter, the considerations reported above indicate, at least in principle, the usefullness of applying electrochemical methods based on pH measurements to the estimation of the concentration of many chemical species of physiological interest, such as urea, glucose, uric acid, etc. It should be added that the estimation of the amount of hydrogen ions released or absorbed in a chemical reaction by pH electrode measurements can be obtained irrespectively of the optical quality of the sample, which severely limits the application of spectrophotometric methods to the study of whole blood or other turbid solutions.

A close analysis of the analytical instrumentation so far commercially produced shows, however, that no instruments of practical use suitable for the determination of substrates or enzymes in solution using the pH measurement approach have yet been made available.

This is not surprising since a more detailed analysis of the problem does indeed reveal several practical difficulties. These can be summarized as follows.

(a) The buffer power of samples such as blood or plasma obtained from different individuals is not constant. Thus the estimation of $\Delta[H^+]$ produced in a chemical reaction from the measurement of pH requires an accurate estimate of the buffer power of the sample or, alternatively, that the buffer power of the sample be made negligible compared with the buffer power of the medium where the reaction is made to occur.

(b) Most commercial analyzers based, for instance, on light absorption measurements require a few microliters only of sample solution, which is conveniently diluted into a more sizable (0.5 to 3.0 ml) volume of reagent solution. Application of a similar dilution step would also be necessary prior to pH measurement, but unfortunately would proportionally decrease the concentration of the substance to be determined and the size of the $\Delta$pH measurement. Thus dilution of a blood containing $5.0 \times 10^{-3}$ moles per liter glucose in a 1:100 ratio would reduce the concentration of the glucose to $5 \times 10^{-5}$ moles/liter. Addition of glucose oxidase as per reaction (1) would then release a maximum amount of $5 \times 10^{-5}$ moles/liter of hydrogen ions. In a medium with a buffer equal to $5 \times 10^{-3}$ moles/liter per pH unit, which is a minimum figure if accurate pH measurements are to be made, this would cause of change in pH of $5 \times 10^{-5}/5 \times 10^{-3} = 0.01$ pH units, far too small to be measured accurately with an error of a few percent by available techniques.

(c) pH measurements to $\pm 0.0001$ pH units required to obtain the concentration of glucose would also necessitate a high stability in the temperature of the measuring electrodes and of the solutions, adding further complications to the pH measurement approach.

More recently, an electrometric method for the measurement of small pH changes down to $\pm 5 \times 10^{-5}$ pH units, in biological solutions, has been reported by Luzzana et al, *Anal. Biochem.*, 43:556-563, 1971. The technique is based on the use of two glass electrodes, one of which is used as a reference electrode. This approach has the advantage of eliminating (a) spurious pH drifts due to side reactions frequently found in biological samples, and (b) variations in junction potentials which are known to occur, in the traditional approach of pH measurement using a pH glass electrode and a calomel reference electrode, at the junction between saturated KCl solutions of the reference electrode and the solution under measurement.

Although the principle outlined by Luzzana et al has found several interesting applications in the specialized field of biochemistry, no practical commercial application of this principle has yet been described. This again was to be expected since all described applications of this technique have been, before the disclosure of the present invention, far from simple enough to be used by nonspecialized personnel. The main difficulties in the prior art can be traced to the following points: (a) the two glass electrodes in the apparatus described by Luzzana et al are located in separate compartments which have to be accurately thermostatted to obtain the required stability in reading; (b) the renewal of fresh test solutions in contact with the two electrodes could not be accomplished automatically and required at least a few minutes of manual operations; (c) the volume of the reactions required for each single measurement was at least 10 ml, thus preventing the use of microsamples of the solution under tests; (d) the junction solution between the two test solutions could not be renewed automatically; and (e) all calculations required to obtain the concentration of a given substance under test from the measured values of pH had to be obtained by hand calculation. The present invention overcomes such difficulties, making possible the development of an entirely new apparatus which can automatically estimate the concentration of many substances of interest in the field of clinical chemistry, biochemistry and analytical chemistry.

According to the present invention, the pH of (a) a solution containing the substance of interest and (b) of the same solution to which a small amount of a specific reagent such as, for example, an enzyme, has been added, is measured by two pH electrodes. The difference in pH between the two solutions ($\Delta$pH), when corrected for small blank effects due to the addition of reagents, is free from aspecific drifts in pH and is related only to the effect of the specific reaction. Since under appropriate conditions $\Delta$pH is a function of the amount of $\Delta[H^+]$, i.e. of the hydrogen ions produced or absorbed by the reaction, $\Delta[H^+]$ can be obtained by calculation from $\Delta$pH, whence, from the stoichiometry of the reaction, the concentration of the substance of interest can be determined.

The reagent solution should include a buffer capable of maintaining the reaction medium within a range in which the titration curve for the specific reaction is substantially linear. Ordinarily this would be a range of no greater than 1 pH unit and more preferably no greater than 0.5 pH unit, and most preferably within a range of no greater than 0.1 pH unit.

All substances participating in a chemical reaction resulting in an uptake or release of hydrogen ions can be determined by this method and apparatus, which may then find application in many fields such as in clinicochemistry, in the food and beverage industry, in analytical chemistry, etc. Typical substances which may be determined by this technique are glucose, urea, total carbon dioxide, chloride, and generally all metabolites which are connected through the adenosine triphosphate/adenosine diphosphate (ATP/ADP) system and the diphosphopyridine nucleotide and its reduced form (NAD+/NADH) system to a change in hydrogen ion concentration in solution.

The basic components of the apparatus described herein are:

(a) a cuvette which is automatically filled with a known amount of a solution of the substance(s) to be determined;

(b) a cell provided with two glass capillary microelectrodes for the measurement of pH;

(c) means for filling the cuvette with a known amount of solution, for adding a suitable amount of additional reactant(s) and for filling the two pH electrodes with the solution contained in the cuvette before and after the addition of the reactant(s);

(d) a differential analog amplifier, an analog-to-digital converter, a microprocessor run by appropriate instructions, a digital readout and various electrical and electronic accessory circuits to produce a digital indication of the concentration of the substance under test.

Thus the present invention provides a number of advantages over conventional methods of analysis such as those employing colorimetric methods. For example, the present invention employs very stable and durable sensors, i.e., the two pH electrodes, and does not depend on optical measurements. Thus the method and apparatus may be used for the determination of chemical substances in turbid solutions or in solutions of high optical absorbancy such as diluted plasma, blood, syrups, beverages, or products of the food or cosmetic industry. The invention is highly sensitive since a change of ±0.0001 pH units can be easily measured, leading to the determination of substances present in solution at very low concentrations ($10^{-5}$ moles/liter or less).

The invention also used a relatively small number of proven electronic and mechanical components, and under the control of the microprocessor program, it automatically performs all of the analytical steps required for the analysis and gives final results of the concentration of the substance of interest in a digital form. Further, analysis by the invention herein is reproducible to about 2%, and uses microvolumes of the solution to be analysed (10 microliters or less). The complete analysis may be accomplished in about 40 seconds to provide the final results from the beginning of the analysis.

The method of the invention involves use of the formula:

$$[\text{substance}] = \text{FCAL} \times (\Delta pH_c - \Delta pH_b - \Delta pH_o) \quad (6)$$

wherein [substance] represents the concentration of the substance in question, "FCAL" represents a calibration factor which is a combination of $\beta$ and a dilution factor, $\Delta pH_c$ represents the $\Delta pH$ value of the solution after reaction, $\Delta pH_b$ represents the $\Delta pH_b$ value of the solution of the reagents, but without the sample, and $\Delta pH_o$ represents the $\Delta pH$ value indicative of the level of noise and drift of the machine components.

DESCRIPTION OF THE DRAWINGS

The foregoing, as well as other objects and advantages of the present invention will become apparent from a consideration of the following specification and claims, when taken together with the accompanying drawings in which:

DESCRIPTION OF THE INVENTION

Figure 1:
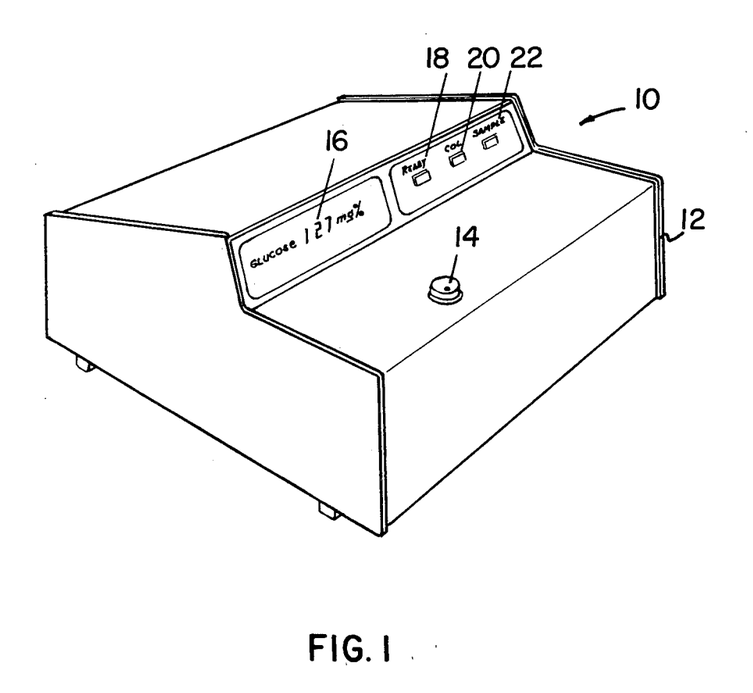
FIG. 1 is a perspective view of the apparatus of the present invention.

Referring first to FIG. 1, the analyzer of the present invention, generally designated 10, is seen to include a housing 12 and is provided with a sample inlet 14 through which the sample being analysed is introduced. A digital display panel 16 is provided to display the results of the analysis, particularly the value of the concentration of the substance under test, in digital form. A lamp 18 is provided to give an indication by the microcomputer when the instrument is ready to accept a sample. Button 20 is used to initiate a cycle of measurements leading to the calibration of the apparatus, and button 22 is used to initiate a cycle of measurements leading to the measurement of the concentration of a given substance under test.

Figure 2:
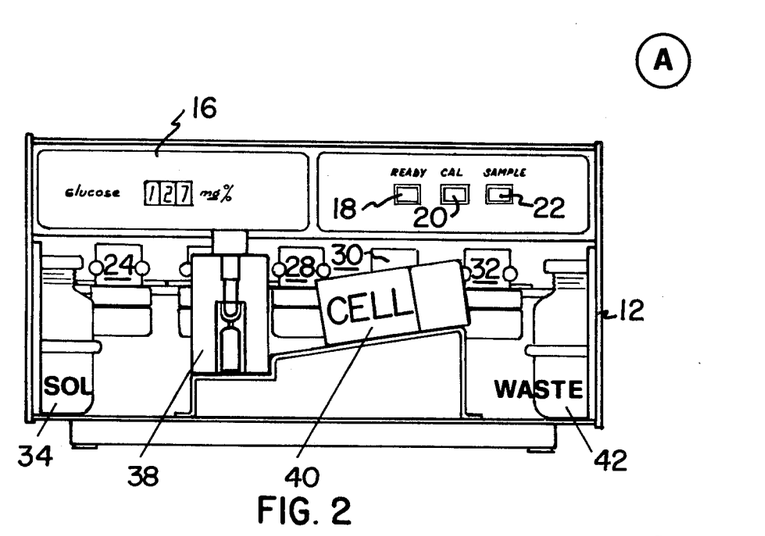
FIG. 2 is a front view of the apparatus of FIG. 1 with the front panel removed.
Figure 3:
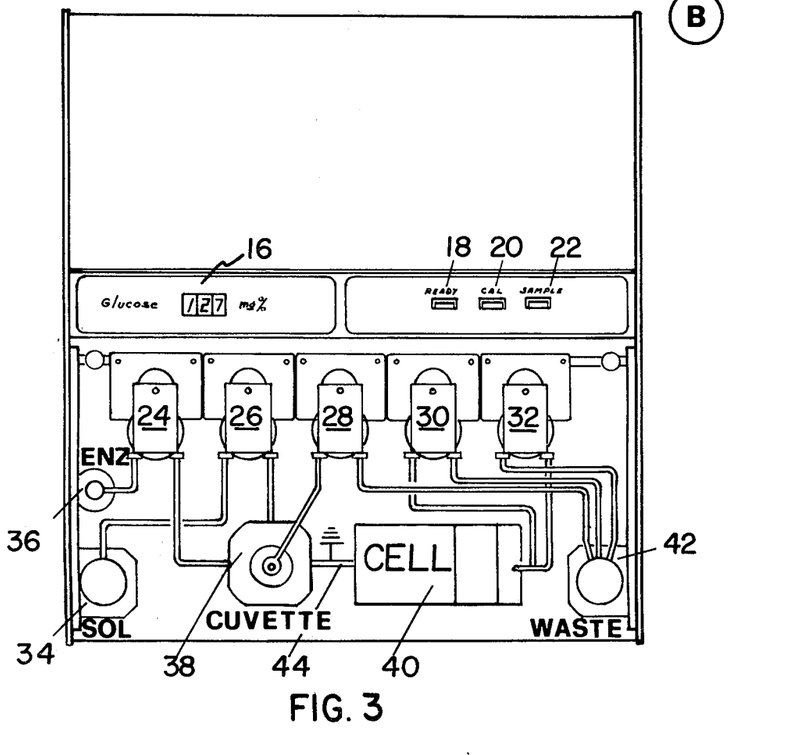
FIG. 3 is a top plan view of the apparatus of the invention with the front panel removed.

FIGS. 2 and 3 show the general layout of the interior of the housing 12 which includes five peristaltic pumps 24, 26, 28, 30 and 32 which, when activated in the proper order by the microcomputer, move, by programmed steps, the solutions contained in solution reservoir 34, enzyme (e.g.) reservoir 36 through the cuvette 38 and cell 40 into the waste container 42. Tubing 44 forms a liquid junction between the two electrodes, as will be seen, and thus should be of a conductive material, preferably stainless steel, and should be at machine ground potential. It should be noted that only when the grounding point is fixed before or at the liquid junction between the two electrodes, and the solution after such point is insulated from ground, is it possible to avoid spurious electrochemical signals and obtain $\Delta pH$ measurements reproducible to ±0.0001 pH units. The other tubing used to connect reservoir 34 and 36, pumps 24–32, cuvette 38, and cell 40, may be any appropriate tubing such as suitable inert plastic or metal tubing.

Figure 4:
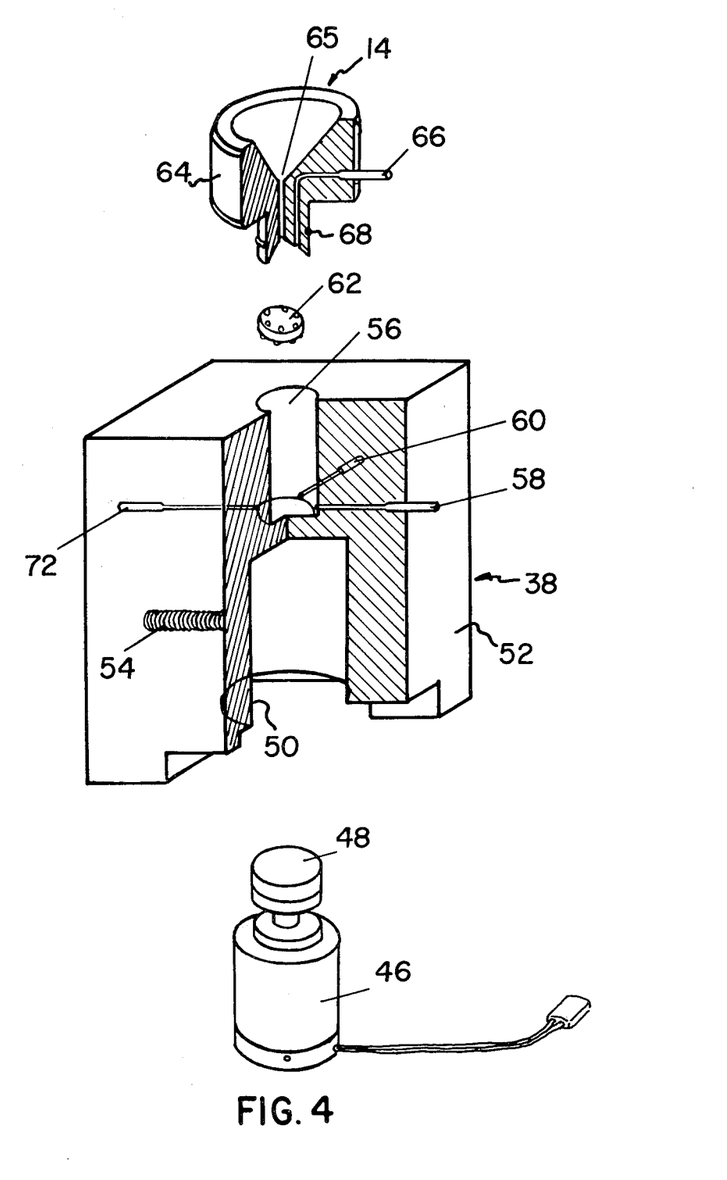
FIG. 4 is an exploded view of the cuvette used in the apparatus of this invention.

Referring now to FIG. 4, the cuvette 38 is seen to include a DC motor 46 which holds a small cylindrical magnet 48. The motor is normally inserted into the circular cavity 50 within block 52 and is held in place by means of a screw inserted into bore 54. A circular cavity 56 is provided in block 52 and may be filled by the peristaltic pump 26 with the solution contained in reservoir 34. A small bore hole 58 is drilled into the block 52 for connecting the cavity 56 with the glass electrodes in cell 40. A similar small bore 60 is provided through which a volume of solution contained in reservoir 34 can be pumped by means of the peristaltic pump 26 into the cavity 56. A circular magnetic stirrer 62 is provided and normally rests at the bottom of the cavity 56 and is magnetically coupled to the motor 46 through the magnet 48. It is used to mix the contents of the cavity 56.

The sample inlet 14 is seen to include a block 64, and is provided with an inlet passageway 65, and a bore 66 is connected via pump 28 to the waste reservoir 42. A suitable seal such as O-ring 68 seals the block 64 within the block 52 since under operating conditions, the block 64 is fully inserted into the cavity 56 of the block 52, thus defining a space of definite volume wherein a chemical reaction may take place. The small passageway 65 is preferably of a diameter of approximately 1.5 mm. A sample contained in a microsyringe or micropipette may be introduced into the cavity 56 through passageway 65. Another bore 72 is provided within block 52 and is connected to reservoir 36 by means of peristaltic pump 24 for introduction of the reagent contained in reservoir 36.

Figure 5:
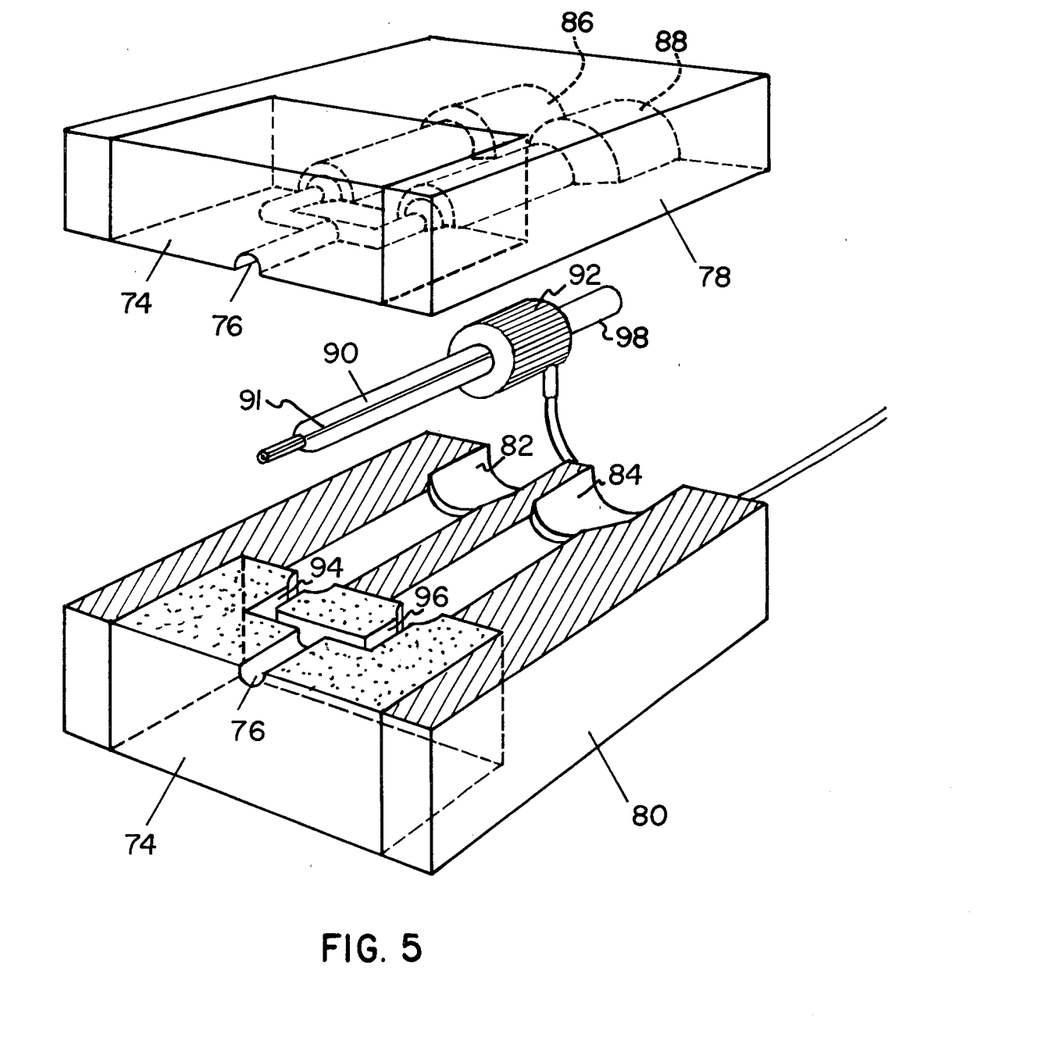
FIG. 5 is an exploded view of the electrode cell used in the apparatus of this invention.

Referring now to FIG. 5, the cell 40 which holds the two capillary glass pH electrodes is shown. Cell 40 comprises a block 74 of plastic material of suitable composition through which appropriate passageways have been drilled as shown. An inlet connection 76 is provided between the cuvette 38 and the two capillary pH electrodes. The cell 40 is formed of two stainless steel blocks 78 and 80 having electrode chamber halves 82, 84, 86 and 88 machined therein. The blocks 78 and 80, although preferably formed of stainless steel, may be formed of any suitable material which has a high temperature transfer coefficient and will insulate and shield the two pH electrodes both magnetically and thermally. This insures uniformity of temperature between the two electrodes.

The electrodes 90, only one of which is shown in FIG. 5, are both of identical construction and are commercially available electrodes, and include a mounting bushing 92 which serves to support the electrodes within the cell 40 and seal one end of the electrode chambers. The solution passes through a capillary passageway 91 in the electrode 90. Solution may be fed to the electrode passageway, and thus through the electrodes, from the inlet passage 76 through the passages 94 and 96. The solution is aspirated by peristaltic pumps 30 and 32 from the reaction chamber or cuvette 38 into cell 40, and flows through the two pH sensitive glass capillary electrodes 90, and via an appropriate length of tubing connected at the end 98 of the electrode to the waste container 42. The connection between the cuvette 38 and the cell inlet 76 is made by a length of capillary stainless steel tubing which is at machine ground potential.

Figure 6:
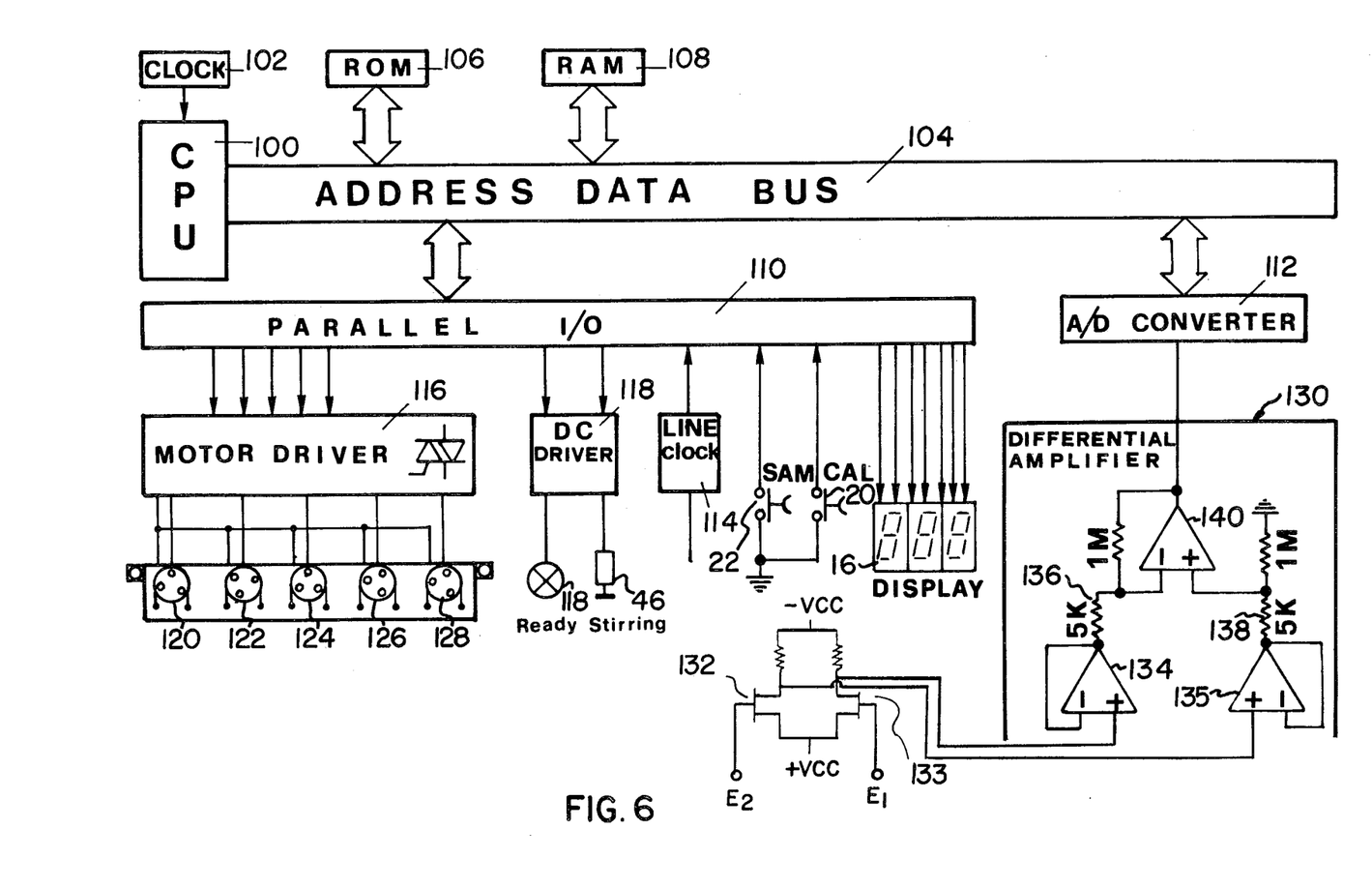
FIG. 6 is a schematic view of the electronic circuit used with the apparatus of this invention.

Referring now to FIG. 6, a schematic illustration of the electronic circuitry used to control the functions of the apparatus is shown. The system is based on a Z80A (Zilog) microprocessor 100 which is run by an appropriate program for data acquisition and elaboration, instrument control, and presentation of results in a known manner. Clock 102 generates a 4 MHz square wave which is sent to the clock input of the Z80A central processing unit (CPU) 100. Address and data lines coming from the CPU 100 are sent to the address data bus 104. This allows the interconnection of the CPU 100 to the read only memory (ROM) 106, the random access memory (RAM) 108, parallel input/output 110 and the analog-digital converter 112. The ROM memory 106 comprises two 2716 EPROM of a total capacity of 4 K bytes, of which approximately 2 K are needed for the mathematical package. Temporary data are stored in the RAM 108, whose size is 500 bytes. The input lines are used to get commands or logic signals as follows: "sample", push button 22; "calibration", push button 20; a line frequency clock 114 which is used to synchronize functions such as start/stop of motors, to start the conversion of the analog to digital converter 112, etc. The output lines are used to provide logic levels to various devices such as the motor driver 116, which drives one or more of the synchronous motors of the peristaltic pumps 24–32, starting the motor when the corresponding line coming from 110 is at a logic level of 1 and stopping the motor when the logic level is 0; (2) the DC driver 118 which turns on the READY light 18 or the stirring motor 46; (3) the display 16, which provides a three digit digital output. This display, according to the logical configuration on its input, can display numbers, or letters A through F to code diagnostic messages by the microprocessor 100, such as "E" for error. The five synchronous motors 120, 122, 124, 126, and 128 are associated with the peristaltic pump 24, 26, 28, 30 and 32 respectively.

The potential difference produced between the two capillary pH electrodes contained in cell 40 is amplified by the differential amplifier circuit 130. The input of the two electrodes shown at terminals $E_1$ and $E_2$ is fed into two low bias current, low drift and high input impedence field effect transistors 132 and 133. To maintain thermal stability, these transistors are preferably contained in a single chip. The output of the two field effect transistors is applied to operational amplifiers 134 and 135, which are connected in a differential amplifier circuit configuration. Their input is applied through two 5000 ohm resistors 136 and 138 respectively, to the negative and positive inputs of an operational amplifier 140. The output of the differential amplifier 130 is then fed into the analog-to-digital converter 112, which is a 12-bit analog-to-digital converter type AD 574 (Analog Devices) with a three state output buffer circuit for direct interface with the address data bus 104. Other similar analog-to-digital converters may of course be employed.

MODE OF OPERATION

In order to demonstrate the description of the analytical capability of the instrumentation of the present invention, reference will be made to the actual measurement of a chemical substances of particular clinical interest, namely the concentration of glucose in plasma. For this purpose, reservoir 34 is filled with a solution containing $25 \times 10^{-3}$ moles/liter phosphate buffer, pH 7.4; $2 \times 10^{-3}$ moles/liter adenosine triphosphate (ATP); and $1 \times 10^{-1}$ moles/liter KCl. Reservoir 36 is filled with a solution containing 0.5 units per microliter of the enzyme hexokinase.

When the instrument is turned on, a sequence of operations is initiated under control of the microprocessor 100. Pump 24 is turned on for an appropriate interval to fill the tube from the enzyme reservoir 36 to the cuvette 38 with fresh solution. Pumps 30 and 32 empty the cuvette 38 through the cell 40. Pump 26 fills the cuvette 38 with an excess of reagent, which completely fills the volume of circular cavity 56. The excess reagent will overflow from cavity 56 into the opening 70, and the excess solution is then removed by pump 28 from the capillary tube 66. In this manner, the volume of the solution contained in cavity 56 is fixed to a defined, predetermined value. After three such cycles of filling and emptying the cuvette, the instrument is ready, and lamp 18 is automatically turned on and the machine is ready to accept two user commands, i.e. calibration or sample measurement. Such commands are initiated by pressing either calibration button 20 or sample button 22.

CALIBRATION CYCLE

The operator next introduces ten microliters of a standard solution containing a known amount of glucose. A typical such standard glucose solution would be 11 mM/liter. The solution is introduced by the use of a micropipette through the sample inlet 14 into the known volume of reagent contained in cavity 56. After introducing the standard, the user presses the calibration button 20 to start the calibration cycle. The standard solution is mixed with the solution contained in cavity 56 by the magnetic stirrer 62 which is magnetically driven by the magnet 48 and the DC motor 46. Half of the solution volume is then aspirated into the two capillary electrodes contained in cell 40 by the action of peristaltic pumps 30 and 32. The output voltage of the electrodes is amplified by the differential amplifier 130, converted by the analog to digital converter 112, and read several times by the microprocessor through the data bus 104, and analyzed to detect the level of noise and drift. The noise level may be affected by, e.g. damaged electrodes, or electrodes which have dried out through extended periods of nonuse. The standard deviation of the data is calculated, and if the noise and drift levels are within predetermined values, no error message is sent to the digital display 16. If the predetermined values are exceded, such as by a severely damaged electrode, an error message is sent to the digital display 16 in order that the operator may take appropriate corrective action before measuring the sample solution. If the quality of the signal is found to be within the predetermined value, a plurality of readings of the difference of potential between the two electrodes, and preferably about 100 readings, are taken, averaged, converted into pH units and stored in the microprocessor RAM 108 as a zero reading ($\Delta pH_o$).

Pump 24 now is started to inject three to four microliters of the enzyme solution contained in reservoir 36 into the cavity 56 followed again by the activation of the motor 46 to mix the enzyme solution with the solution containing glucose remaining in the reservoir 56. The following reaction then commences:

$$ATP + glucose \rightarrow ADP + glucose\text{-}6\text{-}phospate + H^+ \quad (7)$$

The concentrations of ATP and hexokinase are such that reaction (7) is driven, in a few seconds, completely to the right producing a definite amount of hydrogen ions, which amount is proportional to the concentration of glucose in solution. The hydrogen ions liberated by the reaction will cause a change of pH in the solution in accordance with equation (2). Pump 32 is then activated aspirating into the second capillary electrode a volume of the reacted solution. The difference in potential between the two pH glass electrodes respectively containing (1) the glucose solution, and (2) the same solution plus hexokinase is read as described for the zero reading. Again, 100 measurements are taken, averaged, and converted into pH units to give a second reading ($\Delta pH_c$).

A cycle in which all of the foregoing operations are automatically performed by the instrument, but omitting the introduction of the standard solution of glucose, and including addition of the enzyme, is then performed, and a third $\Delta pH$ reading, $\Delta pH_b$, is obtained and stored in the RAM 108. At the end of the calibration cycle, the microprocessor 100 commands a series of three washing cycles. For the first two of these cycles, the reservoir 56 is filled with an appropriate amount of fresh reagent solution from reservoir 34, emptying the cavity 56, and washing the two capillary electrodes, via the peristaltic pumps 30 and 32. The last cycle consists of filling the cavity 56 by the peristaltic pump 26, and removing the excess reagent with the peristaltic pump 28. READY lamp 18 is then turned on to signal the operator that the instrument is ready to accept a sample.

Since in the equation:

$$[\text{standard glucose}] = FCAL \times (\Delta pH_c - \Delta pH_b - \Delta pH_o) \quad (8)$$

all other terms are known, the calibration factor FCAL is automatically calculated and stored in the RAM 108.

SAMPLE CYCLE

After calibration, the operator introduces into fresh reagent contained in cavity 56, 10 microliters of a solution containing an unknown amount of glucose. The solution may be undiluted plasma, whole blood, urine, or any other biological fluid containing or suspected of containing glucose.

Next, the operator presses the sample button 22, and the cycle of operations and measurements as described under "Calibration Cycle" is repeated, obtaining $\Delta pH_o'$ and $\Delta pH_c'$ as in the calibration step. $\Delta pH_b$ is assumed to be the same, to a first order of approximation, as the value obtained in the calibration steps. Since it can be shown that under the experimental conditions described:

$$[\text{sample glucose}] = FCAL \times (\Delta pH_c' - \Delta pH_b' - \Delta pH_o') \quad (9)$$

and all terms on the righthand side of equation (9) have been determined, the concentration of the glucose in the sample may be calculated and presented in digital form on the display panel 16.

Table 1 shows determination of glucose concentration in human plasma as determined by the present invention and by a U.S. Food and Drug Administration proposed manual method of determination using a spectrophotometric procedure (*Federal Register*, Vol. 39, No. 126, June 28, 1974). Similar results were obtained on samples of whole blood from normal and pathological individuals.

| (a) Sample no. | (a) Measured value | (b) Sample no. | (b) Measured value (mg %) |
|---|---|---|---|
| 1 | 113% | 1 | 245% |
| 2 | 112 | 2 | 242 |
| 3 | 110 | 3 | 242 |
| 4 | 112 | 4 | 241 |
| 5 | 109 | 5 | 242 |
| 6 | 109 | 6 | 244 |
| 7 | 112 | 7 | 242 |
| 8 | 116 | 8 | 241 |
| 9 | 112 | 9 | 243 |
| 10 | 111 | 10 | 242 |
| 11 | 109 | 11 | 244 |
| 12 | 111 | 12 | 241 |
| 13 | 112 | 13 | 245 |
| 14 | 112 | 14 | 242 |
| 15 | 110 | 15 | 243 |
| 16 | 112 | 16 | 244 |
| 17 | 112 | 17 | 246 |
| 18 | 112 | 18 | 243 |
| 19 | 114 | | |
| 20 | 111 | | |
| n = 20 | avg. 111.6 ± 1.70 (S.E. ± 1.5%) | n = 18 | avg. 242.9 ± 1.49 (S.E. = 0.61%) |

Values obtained by the FDA suggested hexokinase/-glucose-6-phosphate dehydrogenase manual test (by spectrophotometry) were 110 mg% for sample (a) and 240 mg% for sample (b). It should be added that in this series of experiments $\Delta pH$ of 0.0001 pH units corresponds to the change in pH given by about 1 mg% glucose.

To indicate the linearity of the instrument described in this application, determinations of glucose concentration in aqueous standard solutions containing a known nominal glucose concentration of 50, 100, 200, 500, and 1,000 mg% were also obtained. When the instrument was calibrated with the standard solution containing 200 mg% glucose it gave the following estimations of the concentration of the other solutions:

| Soln 50 | Soln 100 | Soln 200 | Soln 500 | Soln 1000 mg % |
|---|---|---|---|---|
| 48.6 | 98.1 | 198.7 | 511.9 | 1018.0 |
| 51.0 | 100.9 | 200.3 | 504.8 | 1008.0 |

On another series of 25 determinations on the same standard solutions, all points fitted a line given by the equation $y = 1.00X - 0.57$. The regression coefficient found was $r = 0.99$.

The data presented illustrate the accuracy and precision of the invention described. It should be noted that most other commercial instrumentation applying different principles of analysis do not give meaningful results when the glucose concentration of the solution under test exceed about 350 mg%. The instrument described herein is linear at least up to a glucose concentration of 1000 mg%, a value 10 times higher than that found in normal individuals.

While the invention has been described with respect to the determination of glucose, the invention is not limited to such a determination, and in fact a similar set of operations and measurements may be performed, leading to the determination of any other substance of interest. For determination of such other substance, (1) a reaction must be chosen by which the substance of interest is involved in a chemical reaction leading to the liberation of hydrogen ions; (2) the specificity of the reaction must be secured by the addition of a suitable reactant, and (3) the reaction should occur in a buffered medium where pH changes are linear. A suitable reactant may be an enzyme or a chemical agent specific for the substance to be determined. As a further example, an enzyme may be determined by use of a substrate reactant for such enzyme.

The method and instrumentation described herein can thus be used to determine the concentration of chemical substances such as urea, uric acid, proteolytic enzymes, lactic acid pyruvate, and, in general, substances involved in a chain of reactions involving ATP-/ADP or NAD/NADH coenzymes. The method and apparatus also allows the direct estimation of substances such as glucose, urea, alcohol, cholesterol, etc. in turbid solutions such as whole blood, thus avoiding the lengthy and tedious process of red cell precipitation or centrifugation, and the many analytical steps required for obtaining an estimate of the concentration of such substances.

While this invention has been described as having a preferred design, it will be understood that it is capable of further modification. This application, is therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. An analyzer for the quantitative determination of a substance in a simple solution based upon a change of pH of the solution comprising:
   a sample cuvette,
   means for filling said cuvette with a known volume of said sample solution,
   means for adding a reactant to the sample solution in said cuvette for reacting with said substance and producing a change in hydrogen ion concentration,
   a cell having two glass capillary electrodes each for the measurement of pH,
   means for selectively transferring solution from said cuvette to said electrodes before and after addition of a reactant through a common supply conduit connected to said cell,
   said supply conduit being of an electrically conductive material and forming a liquid junction between said electrodes and being at machine ground potential,
   electronic means for processing the pH measurements made by said electrodes and producing a digital indication of the concentration of said substance in said sample solution.

2. An analyzer as in claim 1 and wherein said reactant adding means includes a first peristaltic pump.

3. An analyzer as in claim 1 and wherein said solution transferring means comprises second and third peristaltic pumps each connected to one of said electrodes for selectively drawing solution into one or the other of said electrodes.

4. An analyzer as in claim 1 and wherein said cell comprises a housing having passages therein for supporting said electrodes.

5. An analyzer as in claim 1 and including an electrically non-conducting block disposed in said housing and having a fluid passage in communication with each of said electrodes and with said supply conduit.

6. An analyzer as in claim 5 and wherein said housing has a high temperature transfer coefficient so as to maintain uniformity of temperature of said electrodes.

7. An analyzer as in claim 1 and wherein said electronic means includes amplifier means connected to said electrodes for generating an electrical signal as a function of the pH difference between said electrodes.

8. An analyzer as in claim 7 and wherein said amplifier means comprises a different amplifier.

9. An analyzer as in claim 8 and wherein said electronic means further includes an analog-to-digital convertor for receiving the output from said differential amplifier and supplying a representative signal to a central processing unit for display of the concentration of said substance.

10. An analyzer for the quantitative determination of a substance in a sample solution based upon a change of pH of the solution comprising:
    a cuvette having a plurality of inlet passages and a single outlet passage,
    an electrode cell housing having two electrode supporting passages,
    a glass capillary electrode in each of said supporting passages each for measuring pH of solution therein,
    a fluid passage formed in an electrically non-conducting portion of said housing and connecting with each of said electrodes,
    conduit means connecting said outlet passage and said fluid passage, said conduit means being electrically conductive and at machine ground potential whereby said conduit means and said fluid passage form a liquid junction at machine ground potential,
    means connected to said electrodes for selectively drawing solution from said cuvette to one or the other of said electrodes, and
    electronic means for processing the pH measurements made by said electrodes and producing a digital readout of the concentration of said substance in said sample solution.

* * * * *